United States Patent [19]
Haddad et al.

[11] Patent Number: 4,855,270
[45] Date of Patent: * Aug. 8, 1989

[54] BORONAARONATE MOLECULAR SIEVE

[75] Inventors: Muin S. Haddad, Naperville; John J. Schimandle, Coal City, both of Ill.

[73] Assignee: Amoco Corporation, Chicago, Ill.

[*] Notice: The portion of the term of this patent subsequent to Jan. 26, 2005 has been disclaimed.

[21] Appl. No.: 65,400

[22] Filed: Jun. 23, 1987

Related U.S. Application Data

[63] Continuation of Ser. No. 824,422, Jan. 31, 1986, Pat. No. 4,721,607.

[51] Int. Cl.$^4$ .................. B01J 29/04; B01J 29/06; C01D 33/26
[52] U.S. Cl. .................. 502/64; 502/202; 423/277; 423/279; 423/326; 423/329
[58] Field of Search .............. 423/277, 326, 325, 328, 423/329, 330; 502/60, 62, 77, 202

[56] References Cited

U.S. PATENT DOCUMENTS

| | | | |
|---|---|---|---|
| 4,049,573 | 9/1977 | Kaeding | 502/77 |
| 4,495,303 | 1/1985 | Kuehl | 502/62 |
| 4,514,516 | 4/1985 | Puskas | 502/202 |
| 4,605,805 | 8/1986 | Chang et al. | 585/415 |
| 4,650,654 | 3/1987 | Arika et al. | 423/328 |
| 4,656,016 | 4/1987 | Taramasso et al. | 423/277 |
| 4,708,857 | 11/1987 | Leen et al. | 423/326 |
| 4,721,607 | 1/1988 | Haddad et al. | 423/277 |

FOREIGN PATENT DOCUMENTS

| | | | |
|---|---|---|---|
| 0049386 | 4/1982 | European Pat. Off. | 423/328 |
| 0055529 | 7/1982 | European Pat. Off. | 423/328 |
| 0103981 | 3/1984 | European Pat. Off. | 423/328 |

OTHER PUBLICATIONS

Gies et al., "One-Step Synthesis, Properties and Crystal Structure of Aluminum-Free Ferrierite", Zeolites, 7, 9/1987.

*Primary Examiner*—Anthony McFarlane
*Attorney, Agent, or Firm*—William H. Magidson; Ralph C. Medhurst

[57] ABSTRACT

A new crystalline borosilicate molecular sieve, boronaaronate, having a composition in terms of mole ratios of oxides:

$$0.9 \pm 0.2 M_{2/n}O:B_2O_3:ySiO_2:zH_2O$$

wherein M is a cation of valence n, y is between 2 and about 700, and z is between 0 and about 200, and having a characteristic X-ray diffraction pattern. The boronaaronate is prepared by reacting under crystallization conditions, in substantial absence of a metal hydroxide, an aqueous mixture containing an oxide of silicon, an oxide of boron, ethylenediamine, and an organic material comprised of a heterocyclic nitrogen-containing aromatic compound or an aliphataic alcohol. Boronaaronate is useful in hydrocarbon conversion processes.

30 Claims, No Drawings

BORONAARONATE MOLECULAR SIEVE

This is a continuation of application Ser. No. 824,422, filed Jan. 31, 1986 now U.S. Pat. No. 4,721,607 issued Jan. 26, 1988.

This invention relates to a crystalline borosilicate molecular sieve having a crystalline topology similar to ferrierite aluminosilicate. The crystalline borosilicate molecular sieve is prepared by reacting under crystallization conditions, in substantial absence of a metal hydroxide, an aqueous mixture containing an oxide of silicon, an oxide of boron, ethylenediamine, and a heterocyclic nitrogen-containing aromatic compound or an aliphatic alcohol.

Some zeolitic materials, both natural and synthetic, are known to have catalytic capabilities for many hydrocarbon processes. Zeolitic materials typically are ordered porous crystalline aluminosilicates having a definite structure with cavities interconnected by channels. The cavities and channels throughout the crystalline material generally are uniform in size which sometimes permits selective separation of hydrocarbons. Consequently, these materials, in many instances, are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. Negative framework charge resulting from substitution of an aluminum atom for a silicon atom is balanced by positive ions, for example, alkali-metal or alkaline-earth-metal cations, ammonium ions, or hydrogen alkaline-earth-metal cations, ammonium ions, or hydrogen ions.

Molecular sieves characterized as "ferrierite" by chemical composition and X-ray spectrum are known as naturally occurring materials and as synthesized materials. A ferrierite sieve is characterized as a crystalline aluminosilicate typically having a silica/alumina molar ratio of 2 to 40 and having a distinctive X-ray pattern.

A conventional ferrierite sieve is produced by crystallizing a basic mixture of sodium aluminate and an oxide of silicon without the use of an organic template compound. Such ferrierites are described in D. W. Breck "Zeolite Molecular Sieves," John Wiley & Sons, 1974, incorporated by reference herein. U.S. Pat. No. 4,000,248 discloses a method of producing a ferrierite molecular sieve using N-methyl pyridinium hydroxide as an organic template compound in the crystallization of the sieve. U.S. Pat. Nos. 4,016,245, 4,107,195, and 4,046,859 disclose the formation of a ferrierite-like material using an organic template derived from ethylenediamine, pyrrolidine or butanediamine, or organometallic 2-(hydroxyalkyl)- trialkylaluminum compounds.

U.S. Pat. No. 4,251,499 discloses the preparation of synthetic ferrierite in the presence of piperidine or an alkyl-substituted piperidine. The reference specifically states that when other heterocyclic compounds such as pyridine are used "either no ferrierite at all is formed, or the ferrierite obtained is highly contaminated with other zeolitic and/or amorphous material." U.S. Pat. No. 4,377,502 discloses the ues of oxygen-containing organic templates such as ethers and hydroxy amines in the preparation of aluminosilicate ferrierite molecular sieves.

Boron is not considered a replacement for aluminum or silicon in a zeolitic composition. Although over a hundred aluminosilicate zeolites are listed by Breck, the text states that "actual incorporation of boron in a zeolite structure has not been achieved." However, a new crystalline borosilicate molecular sieve AMS-1B was disclosed in U.S. Pat. Nos. 4,268,420 and 4,269,813, incorporated by reference herein. According to these patents AMS-1B can be synthesized by crystallizing a source of an oxide of silicon, an oxide of boron, an oxide of sodium, and an organic template compound such as a tetra-n-propylammonium salt. In order to form a catalytically-active species of AMS-1B, sodium ion typically is removed by one or more exchanges with ammonium ion followed by calcination. Other methods to produce borosilicate molecular sieves include formation of a borosilicate using ethylenediamine with sodium hydroxide disclosed in British Patent Application No. 2,024,790. Despite discoveries of borosilicates with crystalline structures, the formation of crystalline borosilicates remains unpredictable. The reaction mechanisms whereby reaction gels are converted into crystalline borosilicates are not sufficiently well known to suggest to one skilled in the art the reaction compositions and formulation techniques which could reasonably be expected to yield a crystalline borosilicate with an X-ray diffraction pattern similar to that of ferrierite.

The material of this invention is referred to as "boronaaronate", a crystalline borosilicate molecular sieve having a characteristic structure as shown by its X-ray diffraction pattern and composition. Although the X-ray diffraction pattern of the boronaaronate of this invention shows similarities to that of ferrierite aluminosilicate zeolite, which indicates a similar crystalline topology, there are substantive differences between the respective patterns which reflect incorporation of boron into the crystalline framework of the boronaaronate molecular sieve. For example, it is known that the boron-oxygen bond length is shorter than either the silicon-oxygen or aluminum-oxygen length. Thus, a contraction of the crystalline unit cell is expected in a molecular sieve in which boron is incorporated into the framework. Such effect on the unit cell is observed by shifts of lines in the X-ray diffraction pattern of a borosilicate as compared to an aluminosilicate. However, the crystalline boronaaronate of this invention is prepared in substantial absence of aluminum and consequently there may be very little aluminum present in the boronaaronate of this invention. The structure of boronaaronate is distinct from the structures of known crystalline borosilicates.

The object of this invention is to provide a crystalline borosilicate-type material, boronaaronate, having a crystalline topology similar to the topology of ferrierite. Another object of this invention is a method of producing boronaaronate, said method comprising reacting an oxide of silicon, an oxide of boron, ethylenediamine, a heterocyclic nitrogen-containing aromatic compound or an aliphatic alcohol, and water under crystallization conditions. A further object of this invention is a method of hydrocarbon conversion using the boronaaronate described in this invention.

SUMMARY OF THE INVENTION

Boronaaronate, a crystalline borosilicate having a crystalline topology similar to the topology of ferrierite, has been discovered having the following composition in terms of mole ratios of oxides:

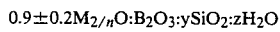

wherein M is at least one cation with the valence of n, y is between about 2 and about 700 or more, preferably between about 5 and about 150, and z is between 0 and about 200, preferably between 0 and 120, having an X-ray diffraction pattern substantially as shown in Table I.

This novel molecular sieve is prepared by a method which comprises reacting under crystallization conditions, an aqueous mixture containing an oxide of boron, a heterocyclic nitrogen-containing aromatic compound or an aliphatic alcohol, ethylenediamine, and an oxide of silicon. The crystalline boronaaronates of this invention are particularly useful in hydrocarbon conversion processes.

DESCRIPTION OF THE INVENTION

The boronaaronate of this invention is a new crystalline borosilicate molecular sieve material having the following composition in terms of mole ratios of oxides:

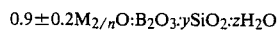

wherein M is at least on cation of valence n, y is between about 2 and about 700 or more, preferably between about 5 and about 150, and z is between 0 and about 200, preferably between 0 and 120, having a low alumina content and having an X-ray diffraction pattern substantially as shown in Table I. M is preferably hydrogen.

Boronaaronate preparations of this invention showing particular catalytic properties have a silica/boria mole ratio of about 15 to about 50.

Another aspect of this invention relates to a method of producing a crystalline boronaaronate by reacting an oxide of boron, an oxide of silicon, ethylenediamine, a heterocyclic aromatic compound or an aliphatic alcohol, and water under crystallization conditions. The crystalline boronaaronates of this invention are useful in hydrocarbon conversion processes and are particularly suitable for isomerization of alkylaromatics such as xylenes.

A typical X-ray diffraction pattern of a boronaaronate molecular sieve of this invention is shown in Table I.

TABLE I

| Interplanar spacings, d[1] | Assigned Strength[2] |
|---|---|
| 9.30 ± 0.20 | S |
| 7.00 ± 0.15 | W |
| 6.85 ± 0.15 | M |
| 6.50 ± 0.15 | W |
| 5.64 ± 0.10 | W |
| 5.58 ± 0.10 | W |
| 3.92 ± 0.08 | M |
| 3.86 ± 0.08 | W |
| 3.78 ± 0.05 | W |
| 3.72 ± 0.05 | W |
| 3.49 ± 0.05 | M |
| 3.42 ± 0.05 | W |
| 3.26 ± 0.05 | W |

TABLE I-continued

| Interplanar spacings, d[1] | Assigned Strength[2] |
|---|---|
| 3.08 ± 0.05 | W |

[1]in Angstroms
[2]per assigned value chart described in Example 1

The boronaaronate molecular sieve of this invention is prepared by reacting, under crystallization conditions, an aqueous mixture containing an oxide of silicon, an oxide of boron, ethylenediamine, and a heterocyclic nitrogen-containing aromatic compound or an aliphatic alcohol.

Examples of oxides of boron are $H_3BO_3$, $B_2O_3$, and $H_3B_3O_6$. Examples of oxides of silicon are silicic acid, sodium silicate, tetraalkyl silicates, and "LUDOX" materials (stabilized polymers of silicic acid [40% solids] manufactured by E. I. du Pont de Nemours & Co.) which include Ludox HS-40 (sodium stabilized) and Ludox AS-40 (ammonia stabilized). Another example is Nalco 2327, an ammonia stabilized colloidal silica [40% solids] manufactured by Nalco Chemical Company.

In addition to ethylenediamine, other organic materials used in this invention include materials such as heterocyclic nitrogen-containing aromatic compounds and aliphatic alcohols or combinations thereof. Typically, suitable nitrogen-containing heterocyclic aromatic compounds contain about 4 to about 9 carbon atoms and at least one nitrogen atom in an aromatic nucleus together with their aryl- and alkyl-substituted derivatives. Examples of the aromatic compounds useful in this invention include pyridine, quinoline, isoquinoline, and pyrrole. Suitable pyridine compounds include pyridine and aryl- or alkyl-substituted pyridines. Pyridine, quinoline, and isoquinoline are the preferred heterocyclic compounds in this invention. Aliphatic alcohols useful in this invention include mono and polyhydroxy alcohols and mixtures of said alcohols. Examples of suitable alcohols include $C_1$–$C_{10}$ alkyl alcohols such as ethanol, propanol, isopropyl alcohol, and butanol or mixtures thereof. Examples of suitable alkylene glycols include ethylene glycol and propylene glycol. Preferred alcohols include ethanol, propanol, and isopropyl alcohol. Ethylene glycol is the preferred glycol. Substitution of other organic compounds such as alkylammonium compounds for the alcohols or aromatic compounds in this invention results in amorphous products or products with distinctly different X-ray diffraction patterns, e.g., AMS-1B crystalline borosilicate molecular sieve.

Preferably, the boronaaronate of this invention is prepared in the substantial absence of alkali or alkaline earth metals or ions; i.e., no alkali or alkaline earth metals or compounds are added during the preparation of the boronaaronate. Although alkali or alkaline earth ions can be present as impurities in the starting materials, it is advantageous that the starting reagents contain as little alkali metal ion contaminant as practicable. When sodium hydroxide was used instead of ethylenediamine in the process of this invention, an amorphous product resulted. Because ethylenediamine is used as the base, the crystalline borosilicate of this invention requires no ion-exchange procedure before formulation into a catalytic composition. However, if an alkali metal cation is desired, it can be placed in the boronaaronate by ion exchange after it is formed.

The mole ratios of the various reactants can be varied considerably to produce the boronaaronates of this invention. Generally in preparations according to this invention, the mole ratio of silica source to boria source may range from about 1 to about 150; the mole ratio of water to silica may range from about 1 to about 100 or higher, the mole ratio of ethylenediamine to silica may range from about 0.05 to about 5 or higher, and the mole ratio of a suitable aromatic compound or alcohol to silica may range from about 0.1 to about 10 or higher. Typically, preferred mole ratios of the initial reactant concentrations for producing boronaaronate can vary as indicated in Table II:

TABLE II

| Mole Ratios | Preferred | Most Preferred |
|---|---|---|
| Silica/Boria | 2–150 | 4–20 |
| $H_2O/SiO_2$ | 15–80 | 20–40 |
| $EDA/SiO_2$ | 0.2–2.0 | 0.8–1.6 |
| Aromatic compound/$SiO_2$ | 0.2–3.0 | 0.3–2.0 |
| Alcohol/$SiO_2$ | 0.4–4.0 | 0.6–2.6 |

It is possible to vary the $SiO_2/B_2O_3$ molar ratio in the final product in a range of about 2 to about 700, preferably about 4 to about 300, and most preferably about 5 to about 150 or more by varying the quantity of the boron-containing reactant in the reaction mixture. A molar excess of boria to silica typically is needed to produce a sieve with a particular boron content.

The molecular sieves of this invention typically have a high $SiO_2/Al_2O_3$ ratio which can range to over 3000:1, typically from about 1000:1 to about 3000:1. The typical ratio for boronaaronate is much higher than $SiO_2/Al_2O_3$ ratios found in the prior art synthetic ferrierite materials and is generally limited only by the availability of aluminum-free raw materials. Because of their high $SiO_2/Al_2O_3$ ratios, boronaaronates are expected to have superior stability characteristics over the prior art ferrierites and to exhibit more hydrophobic surface selectivity.

In another aspect of this invention, molecular sieves with topologies similar to that of ferrierite but having lower aluminum content (higher $SiO_2/Al_2O_3$ ratios) than prior art synthetic ferrierites can be prepared by controlling the amount of aluminum (relative to the amount of boron) present in the starting materials and mixture. Through careful control of the aluminum content in the starting mixture, ferrierite-like molecular sieves with silica/alumina mole ratios above 40, preferably above 100, and most preferably above 300 can be prepared by the process of this invention.

The material of the present invention is prepared by mixing in water (preferably distilled or deionized) ethylenediamine, a boron oxide source, and the alcohol or aromatic compound. The order of addition is typically not critical and a typical procedure is to dissolve ethylenediamine and boric acid in water and then add the alcohol or aromatic compound. Generally, the silicon oxide compound is added with intensive mixing. The resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction system falls within the range of about 8 to about 12 and most preferably between about 9 and about 10.5. The pH is controlled by the concentration of ethylenediamine.

In a more detailed description of a typical preparation of this invention, suitable quantities of ethylenediamine and boric acid ($H_3BO_3$) are dissolved in distilled or deionized water followed by addition of the aromatic compound or aliphatic alcohol. The resulting slurry is transferred to a closed crystallization vessel and reacted usually at a pressure at least the vapor pressure of water for a time sufficient to permit crystallization which usually is about 0.5 to about 100 days, typically is about 2 to about 20 days, and preferably is about 3 to about 14 days, at a temperature maintained below the decomposition temperature ranging from about 100° to about 200° C., preferably about 120° to about 180° C. The crystallizing material can be stirred or agitated as in a rocker bomb. Preferably, the crystallization temperature is maintained below the decomposition temperature of the alcohol or aromatic compound used in the preparation. Especially preferred conditions are crystallizing at about 165° C. for about 2 to about 14 days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25° to 200° C., to form a dry cake which can then be crushed to a powder or to small particles and extruded, pelletized, or made into forms suitable for its intended use. Typically, materials prepared after mild drying contain amounts of the alcohol or aromatic compound and water of hydration within the solid mass. A subsequent activation or calcination procedure is necessary, if it is desired to remove these materials from the final product. Typically, mildly dried product is calcined at temperatures ranging from about 260° to about 850° C. and preferably from about 525° to about 600° C. Extreme calcination temperatures or prolonged crystallization times can prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at about 145°–250° C. for about 16 hours, then calcined in air in a manner such that the temperature rise does not exceed 125° C. per hour until a temperature of about 540° C. is reached. Calcination at this temperature usually is continued for about 4 to 16 hours.

A catalytically active material can be placed onto the boronaaronate structure by ion exchange, impregnation, a combination thereof, or other suitable contact means. The cation, M, in the crystalline boronaaronate is usually hydrogen ion, but can be other cations including metal ions and their amine complexes, alkylammonium ions, ammonium ions, and mixtures thereof by replacing the hydrogen ion, by ion exchange, with these cations. The cation has a valence, n, which can be 1 to 8, preferably 1 to 6, and most preferably 1, 2 or 3. Preferred replacing cations are those which render the crystalline boronaaronate catalytically active, especially for hydrocarbon conversion. Typical catalytically active ions include metal ions of Groups IB, IIA, IIB, IIIA, and VIII, and of manganese, vanadium, chromium, uranium, and rare earth elements. Water soluble salts of catalytically active materials can be impregnated onto the crystalline boronaaronate of this invention. Such catalytically active materials include hydrogen, metals of Groups IB, IIA, IIIA, IVB, VIB, VIIB, and VIII, and rare earth elements.

Ion exchange and impregnation techniques are well known in the art. Typically, an aqueous solution of a cationic species is exchanged one or more times at about 25° to about 100° C. Impregnation of a catalytically active compound on the boronaaronate or on a composition comprising the crystalline boronaaronate suspended in and distributed throughout a matrix of a support material, such as a porous refractory inorganic oxide such as alumina, often results in a suitable catalytic composition. A combination of ion exchange and impregnation can be used. The presence of sodium ion in a composition usually is detrimental to catalytic activity. Catalyst compositions useful in xylene isomerization can be based on hydrogen form sieves or on that prepared by ion exchange with species such as nickelous nitrate or by impregnation with species such as ammonium molybdate.

The amount of additional catalytically active material placed on the boronaaronate can vary from less than 1 wt. % to about 30 wt. %, typically from about 0.05 to about 25 wt. %, depending on the intended use. The optimum amount can be determined by routine experimentation.

The crystalline boronaaronate useful in this invention can be incorporated as a pure material in a catalyst or adsorbent, or may be admixed with or incorporated within various binders or matrix materials depending upon the intended process use. The crystalline boronaaronate can be combined with active or inactive materials, synthetic or naturally-occurring zeolites, as well as inorganic or organic materials which would be useful for binding the boronaaronate. Well-known materials include silica, silica-alumina, alumina, alumina sols, hydrated aluminas, clays such as bentonite or kaoline, or other binders well known in the art. Typically, the boronaaronate is incorporated within a matrix material by blending with a sol of the matrix material and gelling the resulting mixture. Also, solid particles of the boronaaronate and matrix material cn be physically admixed. Typically, such boronaaronate compositions can be pelletized or extruded into useful shapes. The crystalline boronaaronate content can vary from anywhere up to 100 wt. % of the total composition. Catalytic compositions can contain about 0.1 wt. % to about 100 wt. % crystalline boronaaronate and typically contain about 2 wt. % to about 65 wt. % of such material.

Catalytic compositions comprising the crystalline boronaaronate of this invention and a suitable matrix material can be formed by adding a finely-active metal compound to an aqueous sol of gel of the matrix material. The resulting mixture is thoroughly blended and gelled, typically by adding a material such as aqueous ammonia. The resulting gel can be dried and calcined to form a composition in which the crystalline boronaaronate and catalytically active metal compound are distributed throughout the matrix material.

The methods of catalyst formulation in a matrix which are described in U.S. Pat. Nos. 4,268,420, 4,269,813, and European Published Application No. 68,796 (all incorporated by reference herein) can be used to prepare catalytic formulations incorporating boronaaronate.

The boronaaronates prepared according to this invention are useful as catalysts for various hydrocarbon conversion processes and are suitable for chemical adsorption. As used herein, the term hydrocarbon conversion means any changing or altering of the carbon bonding or structure of an organic compound containing at least carbon and hydrogen atoms. Included in hydrocarbon conversion processes are isomerization, oligomerization, polymerization, dehydration, dehydrogenation, alkylation, dealkylation, aromatization, hydrocracking, dewaxing, and the like. Some of the hydrocarbon conversion processes for which the boronarronate appears to have useful catalytic properties are fluidized catalytic cracking; hydrocracking; isomerization of normal paraffins and naphthenes; reforming of naphthas and gasoline-boiling-range feedstocks; isomerization of alkylaromatics, such as xylenes; disproportionation of aromatics, such as toluene, to form mixtures of other more valuable produts including benzene, xylene, and other higher methyl-substituted benzenes, hydrotreating, alkylation, including (a) alkylation of benzenes with ethylene, ethanol, or another ethyl carbonation precursor to yield ethylbenzene, (b) alkylation of benzene or toluene with methanol or another methanol or carbonation precursor to yield xylene, especially p-xylene, or pseudocumene, (c) alkylation of benzene with propylene and (d) alkylation of $C_3$ to $C_5$ paraffins with $C_5$ to $C_3$ olefins, hydrodealkylation; hydrodesulfurization; and hydrodenitrogenation. They are particularly suitable for the isomerization of alkylaromatics, such as xylenes, and for the conversion of ethylbenzene. Boronaaronate catalysts can be used to convert alcohols, such as methanol, to hydrocarbon products, such as aromatics or olefins.

Operating conditions for hydrocarbon conversion broadly comprise a temperature of about 95° to about 540° C., a hydrogen-to-hydrocarbon mole ratio of about 0 to about 20, a weight hourly space velocity (WHSV) of about 0.01 weight unit of feed per hour per weight unit of catalyst ($hr^{-1}$) to about 90 $hr^{-1}$, and a pressure of about 0.1 atmosphere to about 100 atmospheres.

The boronaaronates prepared by this invention are epecially suitable for hydrocarbon isomerization and disproportionation. They are especially useful for liquid- or vapor-phase isomerization of xlyenes. In a preferred process, a boronaaronate-based catalyst converts a hydrocarbon stream containing $C_8$ aromatics by isomerization of xylenes and concurrent conversion of ethylbenzene by hydrodealkylation and disproportionation mechanisms. Advanatageously, the conditions for isomerization of xylenes and conversion of ethylbenzene comprise a temperature of about 250° to about 480° C., a hydrogen-to-hydrocarbon mole ratio of about 1 to about 12, a WHSV of about 1 $hr^{-1}$ to about 20 $hr^{-1}$, and a pressure of about 10 psig to about 500 psig. The preferred conditions for the isomerization of xylenes comprise a temperature of about 315° to about 455° C., a hydrogen-to-hydrocarbon mole ratio of about 2 to about 8, a WHSV of about 1 $hr^{-1}$ to about 10 $hr^{-1}$, and a pressure of about 100 psig to about 300 psig. The choice of catalytically active metals to be placed on the crystalline boronaaronate can be selected from any of those well known in the art. When used as a catalyst in isomerization processes with suitable catalytically-active materials placed on boronaaronate, good selectivities for production of desired isomers are obtained.

When boronaaronate is used as a hydrocracking catalyst, hydrocracking charge stocks can pass over the catalyst at temperatures anywhere from about 260° to about 455° C. or higher using known mole ratios of hydrocarbon to hydrogen and varying pressures anywhere from a few up to many thousands of pounds per square inch or higher. The weight hourly space velocity and other process parameters can be varied consistent with the well-known teachings of the art.

Boronaaronate is also suitable as a reforming catalyst to be used with the appropriate hydrogenation components at well-known reforming conditions including temperatures ranging from about 260° to 565° C. or more, pressures anywhere from a few up to 300 psig to 1,000 psig, and weight hourly space velocities and hydrogen-to-hydrocarbon mole ratios consistent with those well known in the art.

The boronaaronates of this invention can also be used as absorbents to selectively absorb specific isomers or hydrocarbons, in general, from a liquid or vapor stream. For example, selective absorption of branched chain hydrocarbons from cyclic hydrocarbons is possible.

The following examples demonstrate, but are in no way intended to limit the present invention.

EXAMPLE 1

Samples of crystalline boronaaronates according to this invention were prepared by dissolving 26.9 grams of boric acid, 103.4 grams of pyridine, and 140.9 grams ethylenediamine in 980.0 grams of distilled water in a laboratory stirrer. At this point the pH was measured and adjusted to about 9 with ethylenediamine. To this solution, 511.9 grams of Ludox AS-40, an ammonia stabilized colloidal silica (40% solids), were added with vigorous stirring which continued for about 15 minutes after addition. The resulting curdy, gelatinous mixture was placed in a stirred, sealed crystallization vessel and heated to 150° C. for ten days. The resulting crystalline material was recovered by filtration and washed thoroughly with distilled water. The material was then dried for at least four hours at 329° F. (165° C.), heated to 1,000° F. (538° C.) over fours hours and held at that temperature for twelve hours. The temperature was then reduced over four hours from 1,000° F. (538° C.) to 120° F. (49° C.).

The X-ray powder diffraction measurements shown in the following tables were obtained on a Scintag PAD V instrument. Data were collected from 5 to 70 degrees two theta in 0.02 degree steps, with a counting time of 4 sec/step. The radition was Ni-filtered Cu K alpha. Slits on the incident beam were 2 and 4 degrees and slits on the diffracted beam were 0.5 and 0.3 degree. Peaks from K alpha 2 were removed using Scintag's software.

In reporting the results obtained, relative intensities, i.e., relative peak heights, were arbitrarily assigned the following values:

| Relative Peak Height | Assigned Strength |
|---|---|
| less than 10 | VW (very weak) |
| 10–19 | W (weak) |
| 20–39 | M (medium) |
| 40–70 | MS (medium strong) |
| greater than 70 | S (strong) |

These assigned strengths are used throughout this application. It is noted however that relative peak heights may vary from sample to sample and particularly from data taken on different instruments. Thus, an observed relative peak height and corresponding assigned strength should be used as approximations in determining the structure of any particular crystalline material.

An X-ray diffraction spectrum of the preparation was measured and contained the lines specified in Table III.

TABLE III

| Interplanar spacings, d[1] | Relative Intensity $(I/I_o)$[2] | Assigned Strength |
|---|---|---|
| 9.37 | 100 | S |
| 7.01 | 16 | W |
| 6.88 | 25 | M |
| 6.55 | 16 | W |
| 5.64 | 5 | W |
| 5.60 | 8 | W |
| 3.94 | 21 | M |
| 3.88 | 14 | W |
| 3.80 | 8 | W |
| 3.73 | 15 | W |
| 3.50 | 27 | M |
| 3.43 | 19 | W |
| 3.27 | 6 | W |
| 3.10 | 10 | W |

[1] in Angstroms
[2] Relative intensities were calculated as $I/I_o \times 100$, where $I_o$ is the intensity of the strongest recorded peak and I is the value actually read for the particular interplanar spacing.

The catalyst was prepared by dispersing the above calcined sieve in PHF-alumina which is initially an acetic acid stabilized alumina hydrosol containing about 10% $Al_2O_3$. Forty grams of calcined sieve were mixed with sufficient distilled water to fill sieve pores. The wet sieve was then added and thoroughly mixed in a high speed blender with 605 grams of the alumina hydrosol. The mixture was gelled (solidified) with the addition of 60 milliliters of concentrated (28 wt. %) aqueous ammonia. The resulting solid was dried for at least four hours at 329° F. (165° C.), heated to 1,000° F. (538° C.) over four hours, and held at that temperature for four hours. The temperature was then reduced over four hours from 1,000° F. (538° C.) to 120° F. (49° C.). The calcined solid was crushed and sized to 18 to 40 mesh (U.S. Sieve Series).

EXAMPLES 2–4

Four additional samples of the crystalline boronaaronate molecular sieve were prepared in a manner similar to that described for Example 1. All exhibited X-ray patterns contain lines corresponding to those shown in Table I. Details of these preparations are summarized in the following table:

TABLE IV

| | Examples | | | |
|---|---|---|---|---|
| | 2 | 3 | 4 | 5 |
| Reagents | | | | |
| Water (grams) | 982.9 | 979.7 | 979.7 | 979.7 |
| $H_3BO_3$ | 53.8 | 26.9 | 53.8 | 53.8 |
| Ethylenediamine (grams) | 148.6 | 140.9 | 142.7 | 145.2 |
| Pyridine (grams) | 108.3 | 103.4 | — | — |
| Quinoline (grams) | — | — | 177.3 | — |
| Isoquinoline (grams) | — | — | — | 178.4 |
| pH | 10.3 | 10.4 | 11.1 | 11.1 |
| Ludox AS-40 (grams) | 501 | 499 | 499 | 522 |
| pH after Ludox addition | 10.3 | 10.4 | 11.2 | 11.1 |
| Conditions | | | | |
| Digestion Time (days) | 9 | 6 | 13 | 13 |
| Digestion Temperature (°C.) | 150 | 150 | 150 | 150 |
| Product | | | | |
| Mole ratio $SiO_2/B_2O_3$ | 20.7 | 40.4 | 19.9 | 20.7 |

TABLE IV-continued

|  | Examples | | | |
| --- | --- | --- | --- | --- |
|  | 2 | 3 | 4 | 5 |
| Mole ratio SiO$_2$/Al$_2$O$_3$ | 2462 | 2484 | 3000 | 2602 |

The catalyst was prepared by dispersing the above calcined sieve in 756 grams of PHF-alumina which is initially an acetic acid stabilized alumina hydrosol containing about 10% Al$_2$O$_3$. Distilled water (300 grams) was added to 50 grams of calcined sieve to fill sieve pores. The wet sieve was then added and thoroughly mixed with 756 grams of alumina hydrosol. The mixture was gelled by adding 60 milliliters of concentrated (28 wt. %) aqueous ammonia with stirring. The resulting solid was dried for 16 hours in a forced air oven at 200° C. The dried solid was calcined at 485° C. for 12 hours. The calcined solid was crushed to 18/40 mesh (U.S. Sieve Series) Fifteen grams of the 18/40 mesh catalyst were placed in a micro aromatics test unit and preconditioned for two hours at the reactor temperature and pressure at the WCF per hour of hydrogen designated in Tables V and VI. The xylene isomerization test results are summarized in Tables V and VI.

TABLE V

|  |  | Examples | |
| --- | --- | --- | --- |
|  |  | 1 | 3 |
| Conditions |  |  |  |
| Reactor Temp. (°C.) |  | 399 | 441 |
| Reactor Pressure (psig) |  | 200 | 240 |
| Space Velocity (WHSV, hr−1) |  | 5.02 | 3.48 |
| Hydrogen/hydrocarbon (mole ratio) |  | 2.02 | 1.13 |
| Components (wt. %) | Feed |  | Feed |
| Paraffins and Naphthenes | 4.30 | 4.30 | 0.06 | 0.11 |
| Benzene | 0.17 | 0.34 | 0.28 | 0.49 |
| Toluene | 0.30 | 0.39 | 0.28 | 0.31 |
| Ethylbenzene | 15.8 | 15.5 | 13.8 | 13.5 |
| p-Xylene | 8.87 | 11.5 | 10.2 | 13.7 |
| m-Xylene | 47.9 | 45.5 | 13.1 | 49.4 |
| o-Xylene | 22.1 | 21.6 | 22.4 | 22.0 |
| C$_9$+ | 0.56 | 0.87 | 19.9 | 0.49 |
| Results[1] |  |  |  |  |
| PATE |  |  |  |  |
| p-Xylene |  |  | 28.0 | 36.4 |
| m-Xylene |  |  | 34.7 | 39.0 |
| o-Xylene |  |  | 13.8 | 18.7 |
| Ethylbenzene conversion (%) |  |  | 1.5 | 2.0 |
| Xylene Loss (%) |  |  | 0.3 | 0.7 |

[1]PATE = Percent Approach to Theoretical Equilibrium

TABLE VI

|  |  | Examples | |
| --- | --- | --- | --- |
|  |  | 4 | 5 |
| Conditions |  |  |  |
| Reactor Temp. (°C.) |  | 399 | 399 |
| Reactor Pressure (psig) |  | 200 | 200 |
| Space Velocity (WHSV, hr−1) |  | 5.02 | 5.00 |
| Hydrogen/hydrocarbon (mole ratio) |  | 2.03 | 2.09 |
| Components (wt. %) | Feed |  | Feed |
| Paraffins and Naphthenes | 4.30 | 4.44 | 1.19 | 1.37 |
| Benzene | 0.17 | 5.30 | 0.40 | 2.14 |
| Toluene | 0.30 | 3.31 | 1.75 | 2.43 |
| Ethylbenzene | 15.8 | 6.72 | 13.9 | 11.0 |
| p-Xylene | 8.87 | 16.6 | 8.01 | 18.1 |
| m-Xylene | 47.9 | 36.8 | 48.7 | 40.0 |
| o-Xylene | 22.1 | 16.3 | 21.1 | 17.5 |
| C$_9$+ | 0.56 | 10.5 | 4.95 | 7.46 |
| Results[1] |  |  |  |  |
| PATE |  |  |  |  |
| p-Xylene |  |  | 102.2 | 002.9 |
| m-Xylene |  |  | 95.0 | 95.5 |
| o-Xylene |  |  | 117.5 | 127.5 |
| Ethylbenzene conversion (%) |  |  | 57.3 | 21.1 |
| Xylene Loss (%) |  |  | 12.4 | 2.9 |

[1]PATE = Percent Approach to Theoretical Equilibrium

EXAMPLE 6

Ninety-three grams of boric acid, 161 grams of ethylenediamine and 200 grams of isopropyl alcohol were mixed in 700 grams of water. The mixture was homogenized at maximum speed then 500 grams of Nalco 2372 (40% solids) were added and the mixture was homogenized for 5 minutes at maximum speed. The resulting mixture was placed in a stirred, sealed crystallization vessel and heated to 165° C. for 4 days. The resulting crystalline material was recovered by filtration, washed thoroughly with distilled water, and dried in a forced draft oven at 200° C. for 16 hours. The catalyst was prepared according to the procedure described in Example 2.

An example of the X-ray diffraction pattern for the boronaaronate after calcination at 537° C. is presented in Table VII:

TABLE VII

| Interplanar spacings, d[1] | Relative Intensity (I/I$_o$) | Assigned Strength |
| --- | --- | --- |
| 9.24 | 100 | S |
| 6.95 | 21 | M |
| 6.82 | 29 | M |
| 6.49 | 19 | W |
| 5.63 | 6 | W |
| 5.55 | 12 | W |
| 3.91 | 25 | M |
| 3.84 | 22 | M |
| 3.76 | 12 | W |
| 3.70 | 23 | M |
| 3.48 | 42 | MS |
| 3.41 | 29 | M |
| 3.25 | 8 | W |
| 3.07 | 13 | W |

[1]in Angstroms
[2]Relative intensities were calculated as I/I$_o$ × 100, where I$_o$ is the intensity of the strongest recorded peak and I is the value actually read for the particular interplanar spacing.

EXAMPLES 7-9

Four additional samples of the crystalline boronaaronate molecular sieve were prepared in a manner similar to that described in Example 6. All exhibited X-ray patterns containing lines corresponding to those shown in Table I. Details of these preparations are summarized in Table VIII.

TABLE VIII

|  | Examples | | | |
| --- | --- | --- | --- | --- |
|  | 7 | 8 | 9 | 10 |
| Reagents |  |  |  |  |
| Water (grams) | 700 | 700 | 700 | 900 |
| H$_3$BO$_3$ | 93.0 | 93.0 | 93.0 | 93.0 |
| Ethylenediamine (grams) | 161 | 161 | 161 | 161 |
| Ethyl alcohol (grams) | — | — | — | 200 |
| n-propyl alcohol (grams) | 200 | — | — | — |
| Ethylene glycol (grams) | — | 200 | — | — |
| Propylene glycol (grams) | — | — | 200 | — |
| pH | 10.4 | 10.4 | 10.4 | — |

TABLE VIII-continued

|  | Examples | | | |
|---|---|---|---|---|
|  | 7 | 8 | 9 | 10 |
| Nalco 2327 (grams) | 500 | 500 | 500 | 500 |
| pH after Nalco addition | 10.4 | 10.4 | 10.4 | — |
| Conditions |  |  |  |  |
| Digestion Time (days) | 8 | 5 | 7 | 5 |
| Digestion Temperature (°C.) | 165 | 165 | 165 | 165 |
| Product |  |  |  |  |
| Mole ratio $SiO_2:B_2O_3$ | 17.0 | 19.0 | 16.0 | 17.7 |
| Mole ratio $SiO_2:Al_2O_3$ | 1446 | 1851 | 1774 | — |

Catalyst compositions were prepared from these samples and tested in xylene isomerization using procedures similar to those described in Example 1. Results of these tests were summarized in the following tables:

TABLE IX

|  | Examples | |
|---|---|---|
|  | 6 | 7 |
| Conditions |  |  |
| Reactor Temp. (°C.) | 398 | 370 |
| Reactor Pressure (psig) | 200 | 200 |
| Space Velocity (WHSV, hr−1) | 5.01 | 5.11 |
| Hydrogen/hydrocarbon (mole ratio) | 2.02 | 1.98 |
| Contact Time (seconds) | 16.46 | 14.81 |
| Components (wt. %) | Feed | Feed |
| Paraffins and Naphthenes | 1.14 | 1.57 | 1.15 | 1.22 |
| Benzene | 0.41 | 4.04 | 0.41 | 1.41 |
| Toluene | 1.76 | 3.21 | 1.76 | 2.20 |
| Ethylbenzene | 13.9 | 8.39 | 14.0 | 12.4 |
| p-Xylene | 8.00 | 17.3 | 8.00 | 18.4 |
| m-Xylene | 48.7 | 38.1 | 48.7 | 40.5 |
| o-Xylene | 21.1 | 16.7 | 21.0 | 17.4 |
| $C_9+$ | 4.09 | 10.7 | 4.98 | 4.47 |
| Results[1] |  |  |
| PATE |  |  |
| p-Xylene |  | 103.7 |  | 103.6 |
| m-Xylene |  | 96.1 |  | 96.1 |
| o-Xylene |  | 129.1 |  | 125.1 |
| Ethylbenzene conversion (%) |  | 39.8 |  | 11.0 |
| Xylene Loss (%) |  | 7.3 |  | 2.0 |

[1]PATE = Percent Approach to Theoretical Equilibrium

TABLE X

|  | Examples | |
|---|---|---|
|  | 8 | 9 |
| Conditions |  |  |
| Reactor Temp. (°C.) | 398 | 371 |
| Reactor Pressure (psig) | 200 | 200 |
| Space Velocity (WHSV, hr−1) | 5.00 | 5.00 |
| Hydrogen/hydrocarbon (mole ratio) | 1.98 | 2.02 |
| Components (wt. %) | Feed | Feed |
| Paraffins and Naphthenes | 1.26 | 1.31 | 1.08 | 1.21 |
| Benzene | 0.42 | 1.24 | 0.41 | 0.74 |
| Toluene | 1.76 | 2.16 | 1.76 | 1.98 |
| Ethylbenzene | 13.9 | 12.7 | 14.0 | 13.6 |
| p-Xylene | 8.00 | 18.1 | 8.01 | 16.1 |
| m-Xylene | 48.7 | 40.3 | 48.8 | 41.7 |
| o-Xylene | 21.0 | 18.0 | 21.0 | 19.3 |
| $C_9+$ | 4.96 | 6.20 | 4.94 | 5.32 |
| Results[1] |  |  |
| PATE |  |  |
| p-Xylene |  | 101.2 |  | 79.9 |
| m-Xylene |  | 96.8 |  | 86.9 |
| o-Xylene |  | 116.0 |  | 59.4 |
| Ethylbenzene conversion (%) |  | 9.0 |  | 2.5 |
| Xylene Loss (%) |  | 1.7 |  | 0.9 |

[1]PATE = Percent Approach to Theoretical Equilibrium

TABLE XI

|  | Example 10 |
|---|---|
| Conditions |  |
| Reactor Temp. (°C.) | 398 |
| Reactor Pressure (psig) | 200 |
| Space Velocity (WHSV, hr−1) | 4.94 |
| Hydrogen/hydrocarbon (mole ratio) | 1.93 |
| Contact Time (seconds) | 17.70 |
| Components (wt. %) | Feed |
| Paraffins and Naphthenes | 1.16 | 1.30 |
| Benzene | 0.41 | 1.44 |
| Toluene | 1.77 | 2.24 |
| Ethylbenzene | 13.9 | 12.39 |
| p-Xylene | 8.01 | 18.2 |
| m-Xylene | 48.6 | 40.2 |
| o-Xylene | 21.1 | 17.7 |
| $C_9+$ | 5.05 | 6.53 |
| Results[1] |  |
| PATE |  |
| p-Xylene |  | 102.8 |
| m-Xylene |  | 96.5 |
| o-Xylene |  | 123.7 |
| Ethylbenzene conversion (%) |  | 11.09 |
| Xylene Loss (%) |  | 2.02 |

[1]PATE = Percent Approach to Theoretical Equilibrium

What is claimed is:

1. A crystalline molecular sieve identified as boronaaronate having a composition in terms of mole ratios of oxides:

$$0.9 \pm 0.2 M_{2/n}O:B_2O_3:ySiO_2:zH_2O$$

wherein M is a cation of valence n, y is above 2 and z is between 0 and about 200 and having an X-ray diffraction pattern substantially as shown in Table I.

2. The molecular sieve of claim 1 wherein M is hydrogen.

3. The molecular sieve of claim 1 wherein y is between about 2 and about 700.

4. The molecular sieve of claim 1 wherein y is between about 5 and about 150.

5. The molecular sieve of claim 1 wherein z is between 0 and about 120.

6. The molecular sieve of claim 1 which further contains $Al_2O_3$ wherein the $SiO_2/Al_2O_3$ mole ratio is above about 300.

7. A composition comprising the boronaaronate of claim 1 wherein said boronaaronate is incorporated within a suitable matrix material.

8. The composition of claim 7 wherein said matrix material comprises silica, silica-alumina, or alumina.

9. The composition of claim 8 wherein said matrix material comprises silica-alumina, or alumina.

10. The composition of claim 9 wherein y is between about 15 and about 50.

11. The composition of claim 8 wherein the molecular sieve further contains $Al_2O_3$ wherein the $SiO_2/Al_2O_3$ ratio is above about 300 and y is between 5 and about 150.

12. A method for preparing a crystalline molecular sieve composition having in terms of mole ratios of oxides:

$$0.9 \pm 0.2 M_{2/n}O:B_2O_3:ySiO_2:zH_2O$$

wherein M is a cation of valence n, y is between 2 and about 700, and z is between 0 and about 200 and having the X-ray diffraction pattern substantially as shown in Table I which method comprises reacting under crystallization conditions aqueous mixture consisting essentially of an oxide of boron, ethylenediamine, an oxide of silicon, and an organic material comprised of a heterocyclic aromatic compound or an aliphatic alcohol or a combination thereof in the substantial absence of alkali or alkaline earth metal ions wherein said aromatic compound contains about 4 to about 9 carbon atoms and at least one nitrogen atom in the aromatic nucleus.

13. The method of claim 12 wherein the crystallizing mixture is maintained at about 100° C. to about 200° C. for about 2 to about 20 days.

14. The method of claim 13 wherein the crystallizing mixture is maintained at about 120° C. to about 180° C. for about 3 to about 14 days.

15. The method of claim 12 wherein the molecular sieve is incorporated within a suitable matrix material.

16. The method of claim 15 wherein the matrix material comprises silica, silica-alumina, or alumina.

17. The method of claim 12 wherein said organic material comprises a heterocyclic nitrogen-containing aromatic compound and the mole ratio of said compound to silica is between about 0.2 and about 3.0, the mole ratio of silica to oxide of boron is between about 5 and about 150, and the mole ratio of water to silica is between about 15 and about 80.

18. The method of claim 17 wherein the mole ratio of said compound to silica is between about 0.3 and about 2.0, the mole ratio of silica to oxide of boron is between about 15 and about 50, and the mole ratio is water to silica is between about 20 and about 40.

19. The method of claim 17 wherein said heterocyclic nitrogen-containing aromatic compound is selected from pyridine, quinoline, or isoquinoline.

20. The method of claim 19 wherein said compound comprises pyridine.

21. The method of claim 12 wherein said organic material comprises an aliphatic alcohol and the mole ratio of said alcohol to silica is between about 0.4 and about 4.0, the mole ratio of silica to oxide of boron is between about 5 and about 150, and the mole ratio of water to silica is between about 15 and about 80.

22. The method of claim 21 wherein the mole ratio of said alcohol to silica is between about 0.6 and about 2.6, the mole ratio of silica to oxide of boron is between about 15 and about 50, and the mole ratio of water to silica is between about 20 and about 40.

23. The method of claim 21 wherein said alcohol contains 1 to 10 carbon atoms.

24. The method of claim 23 wherein said alcohol comprises a $C_1$ to $C_4$ monohydric alcohol.

25. The method of claim 23 wherein said alcohol comprises a $C_2$ to $C_4$ glycol.

26. The method of claim 12 wherein catalytically active materials are placed onto the boronaaronate structure.

27. The method of claim 26 wherein said materials are selected from the group consisting essentially of catalytically active metal ions, amine complexes of said ions, alkylammonium ions, ammonium ions, and mixtures thereof.

28. The method of claim 26 wherein said materials are placed onto the boronaaronate structure by ion exchange, impregnation, or a combination thereof.

29. The method of claim 17 wherein said heterocyclic compound is an aryl- or alkyl-substituted pyridine having a maximum of 9 carbon atoms.

30. The method of claim 26 wherein said materials are catalytically active water soluble salts.

* * * * *

UNITED STATES PATENT OFFICE
CERTIFICATE OF CORRECTION

Patent No. 4,855,270             Dated August 8, 1989

Inventor(s) Muin S. Haddad and John J. Schimandle

It is certified that error appears in the above-identified patent and that said Letters Patent is hereby corrected as shown below:

| Column | Line | |
|---|---|---|
| Title Page Abstract | 14 | reads "aliphataic" and should read --aliphatic-- |
| 3 | 32 | reads "on" and should read --one-- |
| 7 | 45 | reads "cn" and should read --can-- |
| 8 | 19 | reads "produts" and should read --products-- |
| 11 | 19 | reads "Series) Fifteen" and should read --Series). Fifteen-- |
| 12 | 6 | reads "002.9" and should read --102.9-- |
| 12 | 17 | reads "2372" and should read --2327-- |
| 15 | 32 | reads "is" and should read --of-- |

Signed and Sealed this

Twenty-first Day of August, 1990

Attest:

HARRY F. MANBECK, JR.

Attesting Officer      Commissioner of Patents and Trademarks